(12) United States Patent
Heisig et al.

(10) Patent No.: US 10,299,473 B2
(45) Date of Patent: May 28, 2019

(54) LOW PH PHENOLIC DISINFECTANT WITHOUT PARA TERTIARY AMYLPHENOL

(71) Applicant: AMERICAN STERILIZER COMPANY, Mentor, OH (US)

(72) Inventors: Christopher C. Heisig, Saint Louis, MO (US); Nancy-Hope E. Kaiser, Pontoon Beach, IL (US); Thomas W. Smith, Saint Louis, MO (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 15/908,132

(22) Filed: Feb. 28, 2018

(65) Prior Publication Data

US 2018/0310554 A1 Nov. 1, 2018

Related U.S. Application Data

(60) Provisional application No. 62/491,520, filed on Apr. 28, 2017.

(51) Int. Cl.
| | |
|---|---|
| *A01N 25/22* | (2006.01) |
| *A01N 25/30* | (2006.01) |
| *A01N 31/02* | (2006.01) |
| *A01N 31/08* | (2006.01) |

(52) U.S. Cl.
CPC ............. *A01N 31/08* (2013.01); *A01N 25/22* (2013.01)

(58) Field of Classification Search
CPC ....................................................... A01N 31/08
USPC ......................................................... 514/731
See application file for complete search history.

(56) References Cited

U.S. PATENT DOCUMENTS

| | | |
|---|---|---|
| 5,578,318 A | 11/1996 | Honeycutt |
| 6,802,891 B2 | 10/2004 | Kritzler |
| 7,144,846 B2 * | 12/2006 | Keller .................... A01N 31/08 510/161 |
| 8,206,482 B2 | 6/2012 | Williams et al. |
| 8,236,492 B2 | 8/2012 | McDonnell et al. |
| 8,524,799 B2 | 9/2013 | Kritzler |
| 2005/0032913 A1 | 2/2005 | McDonnell et al. |
| 2005/0256018 A1 | 11/2005 | Keller et al. |
| 2006/0270571 A1 | 11/2006 | Burke et al. |
| 2009/0130739 A1 | 5/2009 | Burke et al. |

* cited by examiner

*Primary Examiner* — Kevin E Weddington
(74) *Attorney, Agent, or Firm* — Hudak, Shunk & Farine Co. LPA

(57) ABSTRACT

The present invention relates to phenol containing disinfectants that have superior broad-spectrum antimicrobial efficacy versus traditional chemistry such as quaternary ammonium-containing disinfectants or aliphatic alcohols. Hydrotropic surfactants are utilized in combination with generally environmentally friendly phenol containing compounds such as ortho-benzyl parachlorophenol (OBPCP), ortho phenylphenol (OPP), or parachloro-meta-cresol (PCMC) in the presence of suitable solvents such as an aliphatic alcohol and also in the presence of an inorganic acid, such as phosphoric acid. The solutions are free of para tertiary amylphenol (PTAP), have a low pH and are very stable with respect to gamma irradiation. They can be used with respect to hard surface disinfection, and also as a tuberculocide, a fungicide, a bactericide, and a virucide.

20 Claims, 3 Drawing Sheets

LOW PH PHENOLIC DISINFECTANT WITHOUT PARA TERTIARY AMYLPHENOL

FIELD OF THE INVENTION

The present invention relates to concentrated phenolic disinfectant solutions that are free of para tertiary amylphenol (PTAP) that has been banned in Europe due to environmental toxicity concerns. The phenolic disinfectants of the present invention comprise ortho phenylphenol, ortho-benzyl parachlorophenol, and parachloro-meta-cresol. Hydrotropic surfactants are utilized such as, sodium octyl sulfate, sodium xylene sulfonate, and sodium caprylyl sulfonate with traditional emulsifying and solubilizing surfactants being excluded since they adversely affect the efficacy of the phenolic disinfectant solution. Hydrophilic acidic surfactants such as dodecyl benzene sulfonic acid can also be used. Other components of the solution comprise solvents such as an aliphatic alcohol, an acid such as phosphoric acid, and water.

BACKGROUND OF THE INVENTION

Heretofore, PTAP has been utilized as a disinfectant but has been banned in Europe and is under scrutiny in the United States with regard to hard surface disinfection because of environmental toxicity concerns. A replacement therefore is thus needed.

U.S. Pat. No. 5,578,318, assigned to Isolyser Co., Inc., relates to a method of producing an absorbent composition. A polymeric material characterized as having surface anionic reactive sites is mixed with a source of multi-valent metal ions to render the polymeric material sorbent of aqueous liquids. A dispersant is then added to form a wet slurry which is subsequently dried to a granular consistency.

U.S. Pat. No. 6,802,891, assigned to Novapharm Research (Australia) Pty. Ltd., relates to air filters including a composition which has a biostatic or biocidal agent adapted to migrate through particulates accumulating in use on the filter. The biocidal agent may have bacteriostatic and/or fungistatic properties and may optionally include a humectant, a surfactant or rheological additive. Compositions for treating filters and methods of reducing airborne contaminants in the air are also disclosed.

U.S. Pat. No. 8,206,482, assigned to Emerson Electric Co., relates to vacuum cleaner filters, in particular replaceable vacuum cleaner filters suitable for both dry and wet/dry type vacuum cleaners are disclosed, as well as systems incorporating the use of such filters and methods for their use. The filters include a plurality of adjacently positioned pleats arranged in a closed circumferential, cylindrically-shaped path, a top end cap having a central orifice capable of constricting a post on a vacuum filter cage, and optionally a molded end ring oppositely-spaced from the top end cap for engagement with the motor housing of a vacuum cleaner.

U.S. Pat. No. 8,524,799, assigned to Novapharm Research (Australia) Pty. Ltd., relates to a biostatic coating comprising a coating composition which on drying produces an intrinsically hydrophobic film. The coating composition includes a biocidal complex A-B in which A is a phenolic biocide and B is selected from polyvinylpyrrolidone ("PVP"), PVP polymers, PVP copolymers, and mixtures thereof. The coating composition for example is selected from acrylic and methacrylic polymer based compositions, acrylic and methacrylic copolymer based compositions, vinyl polymer based compositions, vinyl copolymer based compositions, epoxy resins, epoxy esters, and mixtures thereof. Biocides for use in the invention include complexes of PVP or PVP copolymer with triclosan; diclosan; dichlorophen; orthophenylphenol; orthobenzylparachlorophenol, cresols, xylols, and substituted diphenyl ethers.

U.S. Pat. No. 7,144,846 assigned to STERIS Inc. relates to a low pH disinfectant composition comprises an aqueous composition of a phenolic compound, an organic acid, and/or a dispersing surfactant and/or solvent. The disinfectant solution can be concentrated, or more preferably diluted ready to use.

U.S. Pat. No. 8,236,492 assigned to STERIS Inc. relates to a method of decontaminating a surface or liquid which is contaminated with prions includes treating the surface with a composition which includes one or more phenol. Phenols which are particularly effective include p-chloro-m-xylanol, thymol, triclosan, 4-chloro, 3-methylphenol, pentachlorophenol, hexachlorophene, 2,2-methyl-bis(4-chlorophenol), and p-phenylphenol.

U.S. Patent Application 2006/0270571 relates to compositions and methods for deactivating articles contaminated with nanobacteria, generally comprise a dispersant and/or a dissolution agent, and a deactivator. The methods and compositions of the invention are advantageously utilized to decontaminate and/or sterilize various articles such as medical and manufacturing devices or surfaces.

SUMMARY OF THE INVENTION

The concentrated phenolic disinfectant solutions of the present invention contain various components such as phenolic compounds that have been found to be very effective as disinfectants such as with respect to *Mycobacterium smegmatis* and *Mycobacterium bovis*. In order to solubilize the phenolic compounds, hydrotropic surfactants are utilized and sodium xylene sulfonate (SXS), and sodium caprylyl sulfonate (SCS) have been found to give synergistic results. Various hydrophilic acidic surfactants can also be utilized such as decyl benzene sulfonic acid (DBSA), hexadecyl benzene sulfonic acid, with dodecyl benzene sulfonic acid (DDBSA) being preferred. A disinfectant solution comprises mixing and adding the above components with aliphatic alcohols, an inorganic acid source such as phosphoric acid, and water and forming a low pH broad-spectrum disinfectant as for hard surfaces and also is a tuberculocide, a fungicide, a bactericide, and a virucide. Of course the different weight amount of all of the non-aqueous components and the total weight of the solution is water.

A low pH, gamma-irradiation stable, concentrated phenolic disinfectant solution comprises: ortho phenylphenol in an amount of about 1% to about 15% by weight, ortho-benzyl parachlorophenol in an amount of about 2% to about 25% by weight, or optionally para-chloro-meta-cresol in an amount of about 1% to about 15% by weight, or any combination thereof; at least one hydrotropic surfactant; at least one hydrophilic acidic surfactant; a phosphoric acid; one or more aliphatic alcohols having from $C_1$ to $C_6$ atoms; water, wherein the amount thereof is the weight difference of all other components and 100 wt. %; wherein said phenolic disinfectant solution has a pH of from about 0.5 to about 4.0, and is essentially free of para tertiary amylphenol; wherein said phenolic solution is essentially free of an emulsion surfactant, and a solubilizing surfactant; and wherein the amount of the above components are percent by weight based upon the total weight of said concentrated phenolic disinfection solution.

A process for making a low pH, gamma-irradiation stable, concentrated phenolic disinfectant solution, comprising the steps of: adding together and mixing components comprising; a phenolic disinfectant comprising ortho phenylphenol in an amount from about 1% to about 15% by weight, ortho-benzyl parachlorophenol in an amount from about 2% to about 25% by weight, or parachloro-meta-cresol in an amount from about 1% to about 15% by weight, or any combination thereof; at least one hydrotropic surfactant; at least one hydrophilic acidic surfactant; a phosphoric acid; one or more aliphatic alcohols having from $C_1$ to $C_6$ atoms; and water, wherein the amount thereof is the weight difference of all other components and 100 wt. %; wherein the solution is essentially free of a glycol and a polyglucoside; wherein said phenolic disinfectant solution is essentially free of an emulsion surfactant and a solubilizing surfactant; wherein said phenolic disinfectant solution is essentially free of para tertiary amylphenol; and forming a phenolic disinfectant solution having a pH of from about 0.5 to about 4.0; wherein the amounts of the above components are percent by weight based on the total weight of said concentrated phenolic disinfectant solution.

DETAILED DESCRIPTION OF THE INVENTION

Figure 1:
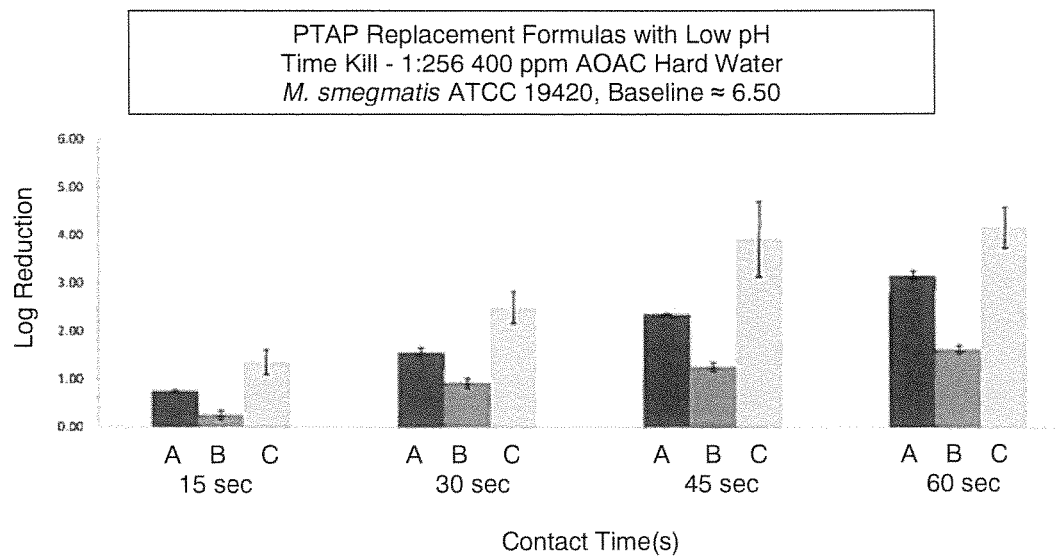
FIG. 1 relates to an embodiment of the present invention and a control containing (PTAP), with respect to time kill of *M. smegmatis;*

The amount of the various components of the present invention is given by weight percent of the active compound based upon the total weight of the concentrated phenolic disinfection solution including water. The amount of water is the weight percent difference of the entire concentrated solution and the total weight percent amounts of all of the various components (excluding water) of the concentrated phenolic disinfectant solution. The invention also relates to the concentrated solutions that have been diluted with water for various applications where low amounts of phenolic disinfectants are suitable. That is, the concentrated solutions of the present invention can be diluted by an amount of water from about 16 to about 512 parts by volume, and desirably from about 64 to about 256 parts by volume for every 1 part by volume of the concentrated phenolic disinfectant solutions of the present invention.

The disinfectant solutions of the present invention contain one or more phenol compounds including orthophenylphenol (OPP), orthobenzyl parachlorophenol (OBPCP), or parachloro-meta-cresol (PCMC), or any combination thereof. With respect to the phenol disinfectants, the amount of the (OPP) is generally from about 1% to about 15%, desirably from about 2% to about 10%, and preferably from about 4% to about 8% by weight based upon the total weight of the phenolic disinfectant solution. The amount of the (OBPCP) is generally from about 2% to about 25%, desirably from about 5% to about 20%, and preferably from about 8% to about 18% by weight based upon the total weight of the phenolic disinfectant solution. A highly preferred (OBPCP) range is from about 14% by weight to about 18% by weight. The amount of the (PCMC) is generally from 1% to about 15%, desirably from 1% to about 10%, and preferably from about 2% to about 8% by weight based upon the total weight of the phenolic disinfectant solution. Generally, the combination of OPP and OBPCP is preferred.

An important aspect of the present invention is the utilization of one or more hydrotropic surfactants that are able to solubilize the various phenol compounds and do not form micelles as do emulsion surfactants. The lack of micelles is important since micelles can tie up the active phenol disinfectants noted above. Thus, the phenolic disinfectant solutions of the present invention are generally free of traditional emulsion surfactants or solubilizing surfactants, or both, that form micelles such as poloxamers, alcohol ethoxylates, or sodium lauryl sulfate, or any combination thereof. Such emulsifying and solubilizing surfactants have also been found to reduce the efficacy of the above-noted phenolic disinfectants as well as reduce gamma irradiation resistant properties thereof. Such surfactants, such as sodium $C_{14}$-$C_{16}$ olefin sulfonate, if utilized, are in a total amount of about 2.0% or 1.0% by weight or less, desirably about 0.01% by weight or less, and preferably nil, that is no emulsion surfactants, or solubilizing surfactants, or both, whatsoever, based upon the total weight of the concentrated phenolic disinfectant solution A desirable class of surfactants include hydrotrope surfactants that comprise sodium xylene sulfonate (SXS), or sodium caprylyl sulfonate (SCS), or sodium octyl sulfate, or any combination thereof. The combination of sodium xylene sulfonate and sodium caprylyl sulfonate is preferred since they have been found to yield synergistic properties with regard to disinfection, especially in the presence of an organic soil, that adds to the broad spectrum disinfectant properties.

The amount of the sodium xylene sulfonate (raw materials, e.g. not diluted) can generally range from about 2% to about 25%, desirably from about 4% to about 20%, and preferably from about 8% to about 15% by weight based upon the total weight of the phenolic disinfectant solution. The amount of the sodium caprylyl sulfonate (raw materials, e.g. not diluted) can be generally from about 1% to about 30%, desirably from about 10% to about 27%, and preferably from about 13% to about 22% by weight based upon the total weight of the phenol disinfectant solution. The amount of the sodium octyl sulfate is from about 1% to about 30%, desirably from about 10% to about 27%, and preferably from about 13% to about 22% by weight based upon the total weight of the phenolic disinfectant solution.

The present invention also contains a hydrophilic acidic surfactant such as decyl benzene sulfonic acid, and hexadecyl benzene sulfonic acid, with dodecyl benzene sulfonic acid being preferred. The total amount of the one or more hydrophilic acidic surfactants is generally from about 1% to about 12%, desirably from about 1% to about 10%, and preferably from about 3% to about 8% by weight based upon the total weight of the phenolic disinfectant solution.

The one or more aliphatic alcohols generally have from 1 to about 6 carbon atoms with ethanol and propanol being preferred, and isopropyl alcohol being highly preferred. The total amount of the one or more alcohols can generally range from about 2% to about 20%, desirably from about 2% to about 18%, and preferably from about 5% to about 15% by weight based upon the total weight of the phenolic disinfectant solution.

While co-solvents, such as glycols having from 2 to about 6 carbon atoms, and surfactants, such as polyglucosides, have been used with various disinfectant solutions, they have been found to adversely affect the efficiency of the concentrated phenolic disinfectant solutions of the present invention with respect to disinfectant properties and reduced resistance to gamma irradiation. Thus, the solutions of the present invention have low amounts of glycols and/or polyglucosides or are free thereof. If utilized, they are in a total amount generally less than about 4% weight, desirably less than about 2% weight, and preferably nil, that is less than about 0.1% by weight of glycols and/or polyglucosides based upon the total weight of said phenolic disinfectant solution.

The inorganic acids of the present invention exclude strong acids such as nitric acid, hydrochloric acid, and sulfuric acid, and any amount thereof is desirably less than about 2%, and preferably less than about 0.5% by weight based upon the total weight of the phenolic disinfectant solution. Phosphoric acid is highly preferred. The total amount of the one or more acids such as phosphoric acid (raw materials, e.g. not diluted), generally ranges from about 5% to about 30%, desirably from about 5% to about 25%, and preferably from about 10% to about 22% by weight based upon the total weight of the phenolic disinfectant solution.

Water is utilized to form a soluble solution, and the amount thereof, as noted above, is the weight difference of the total other components and 100 weight percent, that is, generally from about 10% to about 40%, desirably from about 12% to about 30%, and preferably from about 15% to about 25% by weight based upon the total weight of the concentrated phenolic disinfectant solution. The water is soft water, meaning that water hardness (as calcium carbonate) is less than or equal to 10 parts per million.

In accordance with conventional processes known to the art and to the literature, the phenolic disinfectant solution of the present invention is post gamma-irradiated to render it sterile. For example, it is subjected to gamma-irradiation of about 25 to about 50 kGy with from about 41 to about 47, for example, about 45, being preferred for about 30 to about 3000 minutes. It is also worth noting that gamma-irradiation is also performed to eliminate or reduce the bioburden on the product packaging. The phenolic disinfectants of the present invention such as OBPCP, OPP, and PCMC, are very stable with respect to gamma-irradiation and thus result in sterile solutions.

Desirably, the pH of the phenolic disinfectant solution of the present invention is low, meaning that it ranges from about 0.5 to about 4.0, and preferably is about 0.5. to about 2.0. Low pH is desired because phenolic disinfectants tend to have better antimicrobial efficacy in a low pH range, due to less ionization of phenolic active ingredients in a low pH range.

The invention will be better understood by reference to the following examples which serve to verify the efficacy of the present solution. However, the invention is not limited thereto, but rather by the claims.

FIG. 1 represents kill time with respect to the reduction of M. smegmatis. Improved results were obtained utilizing a formulation of the present invention, i.e. the right column, versus the left column containing commercially marketed product Control containing 7.9% by weight of PTAP, 7.95% OPP. The right-hand column of each of the time tests of FIG. 1 relates to the present invention wherein 6% of OPP is utilized, 13.33% by weight of OBPCP is utilized, and 18.72% by weight of sodium octyl sulfate is utilized along with 20% by weight of phosphoric acid, see Table A. As apparent from FIG. 1, the present invention had a much greater log reduction and time kill values than did the Control.

TABLE A

| Ingredient | Marketed Product - contains 7.9% PTAP and 7.95% OPP | 6% OPP and 10% OBPCP - w/sodium octyl sulfate |
|---|---|---|
| O-phenylphenol | 7.95 | 6.00 |
| Orthobenzyl parachlorophenol (75% active solution) | 0.00 | 13.33 |
| Paratertiary amylphenol | 7.90 | 0.00 |
| Sodium octyl sulfate | N/A | 18.72 |
| Sodium xylene sulfonate | N/A | 10.00 |
| Dodecylbenzene sulfonic acid | N/A | 5.00 |
| Isopropyl alcohol | N/A | 7.70 |
| Phosphoric acid | N/A | 20.00 |
| Soft water | N/A | 19.25 |

Description of the Time Kill Method:

The time kill method is used to determine the $\log_{10}$ reduction of a test organism after being in contact with a test product for a given amount of time. The method is carried out using a test organism suspension to inoculate the test product at Time "0." At specified contact times, an aliquot from the organism/product mixture is transferred into a chemical neutralizer to stop the product interaction. Serial dilutions are performed to obtain a countable range of colony-forming units and aliquots of each dilution are transferred onto agar (growth media) plates. The plates are incubated for a specific length of time and temperature depending on the required growth conditions of the test organism. $\log_{10}$ reductions are calculated by comparing final plate counts to the baseline values. Time kill reference method: ASTM E2315-16, modified in 2016. Standard Guide for Assessment of Antiimicrobial Activity Using a Time-Kill Procedure.

TABLE 1

| Raw Material | A | B | C |
|---|---|---|---|
| | | Wt % | |
| O-phenylphenol | 6.00 | 6.00 | 5.00 |
| Orthobenzyl parachlorophenol (75% active solution) | 17.33 | 17.33 | 17.33 |
| Sodium caprylyl sulfonate | 18.72 | 18.72 | 18.72 |
| Sodium xylene sulfonate | 10.00 | 10.00 | 10.00 |
| Dodecylbenzene sulfonic acid | 5.00 | 5.00 | 5.00 |
| Isopropyl alcohol | 7.70 | 7.70 | 7.70 |
| Phosphoric acid | 15.00 | 15.50 | 16.00 |
| Soft water | 20.25 | 19.75 | 19.25 |

Figure 2:
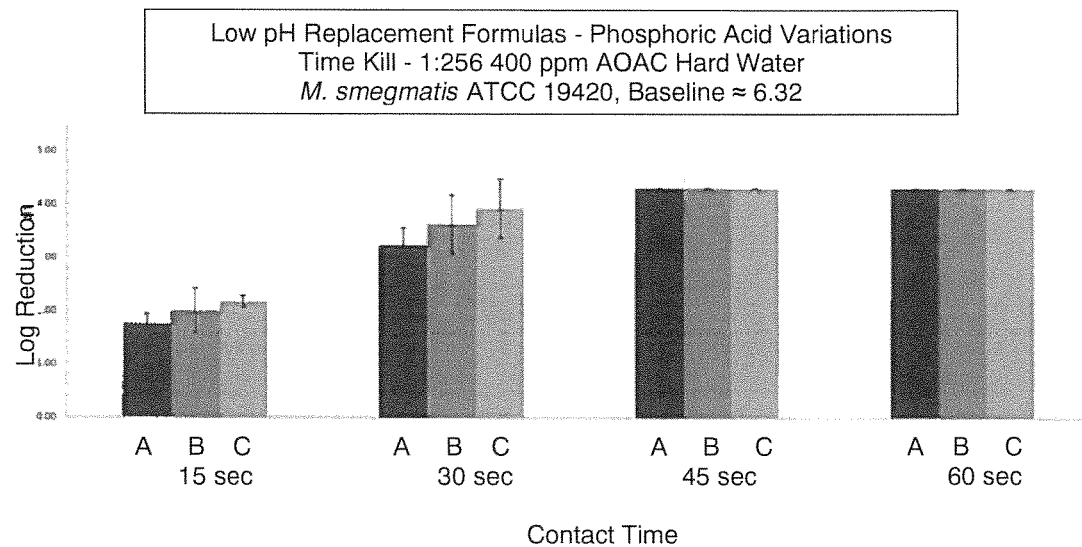
FIG. 2 relates to low pH, PTAP replacement compositions of the present invention having formulations as set forth in Table 1 wherein low time kill values were obtained with respect to *M. smegmatis;*

Table 1 sets forth formulations A, B, and C of the present invention wherein the amount of phosphoric acid was increased. FIG. 2 shows that at short time intervals of testing, higher amounts of phosphoric acid resulted in increased kill or reduction of M. Smegmatis. AOAC 400 ppm hard water refers to water with a hardness level of 400 parts per million (as calcium carbonate). M. smegmatis ATCC 19420 refers to the strain of the Mycobacterium smegmatis organism. Baseline refers to the total growth of the test organism utilized in a particular study. In the case of FIG. 2, the "Baseline=6.32" means that the concentration of the test organism was $10^{6.32}$ colony forming units per milliliter.

Figure 3:
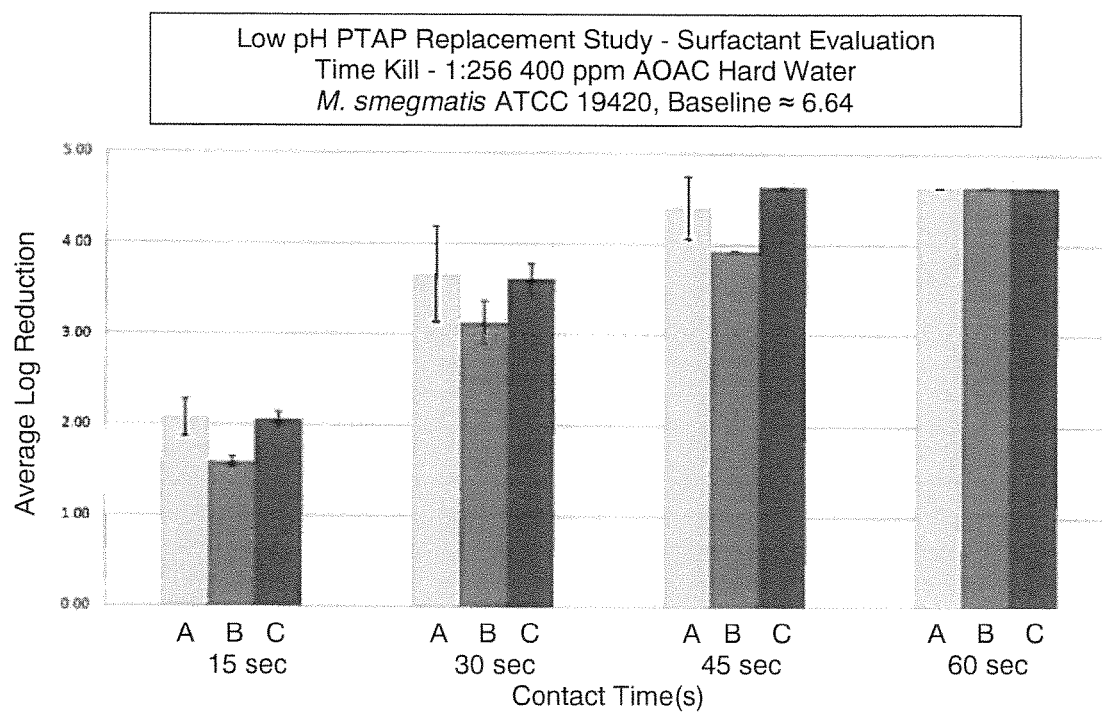
FIG. 3 relates to formulations of the present invention containing different hydrotrope surfactants and a control containing a solubilizing surfactant.

With respect to FIG. 3, the left and right column has good log reduction values but the center column, Formula J, a prior art formulation, using a solubilizing surfactant (control) gave poor results with regard to time kill of M. smegmatis at low pH utilizing the formulations of the present invention.

The formulations of FIG. 3 are set forth in Table B.

TABLE B

| Ingredient | 6% OPP and 10% OBPCP - w/sodium octyl sulfate | 6% OPP and 10% OBPCP - w/sodium olefin sulfonate (Formula J in Table 2) | 6% OPP and 10% OBPCP- w/sodium caprylyl sulfonate (Formula K in Table 2) |
|---|---|---|---|
| | Weight % | | |
| O-phenylphenol | 6.00 | 6.00 | 6.00 |
| Orthobenzyl parachlorophenol (75% active solution) | 13.33 | 13.33 | 13.33 |
| Sodium caprylyl sulfonate | 0.00 | 0.00 | 18.72 |
| Sodium C14-C16 olefin sulfonate | 0.00 | 18.72 | 0.00 |
| Sodium octyl sulfate | 18.72 | 0.00 | 0.00 |
| Sodium xylene sulfonate | 10.00 | 10.00 | 10.00 |
| Dodecylbenzene sulfonic acid | 5.00 | 5.00 | 5.00 |
| Isopropyl alcohol | 7.70 | 7.70 | 7.70 |
| Phosphoric acid | 20.00 | 20.00 | 20.00 |
| Soft water | 19.25 | 19.25 | 19.25 |

Table 2 sets forth different formulations of the present invention utilizing OPP and OBPCP with examples D through G being controls. As set forth in Table 3, the formulations were irradiated in accordance with test method ASTM 51702:2013, Standard Practice for Dosimetry in a Gamma Facility for Radiation Processing, modification date 2013. Irradiation doses were 41-47 kGy (target 45 kGy) for about 300-600 minutes. The phenolic disinfection compositions of the present invention were stable to gamma-irradiation meaning that there was only minor degradation of the phenolic active ingredients (typically, <2% degradation relative to the phenol level prior to irradiation).

TABLE 2

| Raw Material | D | E | F | G | H | I | J | K |
|---|---|---|---|---|---|---|---|---|
| | Weight % | | | | | | | |
| O-phenylphenol | 6.00 | 6.00 | 6.00 | 6.00 | 6.00 | 6.00 | 6.00 | 6.00 |
| Orthobenzyl parachlorophenol (solution) | 13.33 | 17.33 | 17.33 | 17.33 | 17.33 | 13.33 | 13.33 | 13.33 |
| Sodium caprylyl sulfonate | 18.72 | 18.72 | 18.72 | 18.72 | 18.72 | 0.00 | 0.00 | 18.72 |
| Sodium octyl sulfate | 0.00 | 0.00 | 0.00 | 0.00 | 0.00 | 18.72 | 0.00 | 0.00 |
| Sodium C14-16 olefin sulfonate | 0.00 | 0.00 | 0.00 | 0.00 | 0.00 | 0.00 | 18.72 | 0.00 |
| Sodium xylene sulfonate | 10.00 | 10.00 | 10.00 | 10.00 | 10.00 | 10.00 | 10.00 | 10.00 |
| Dodecylbenzene sulfonic acid | 5.00 | 5.00 | 5.00 | 5.00 | 5.00 | 5.00 | 5.00 | 5.00 |
| Isopropyl alcohol | 7.70 | 7.70 | 7.70 | 7.70 | 7.70 | 7.70 | 7.70 | 7.70 |
| Phosphoric acid | 20.00 | 20.00 | 15.00 | 18.00 | 15.00 | 20.00 | 20.00 | 20.00 |
| Hexylene glycol | 2.00 | 2.00 | 2.00 | 2.00 | 0.00 | 0.00 | 0.00 | 0.00 |
| Soft water | 17.25 | 13.25 | 18.25 | 15.25 | 20.25 | 19.25 | 19.25 | 19.25 |

TABLE 3

| Sample | Sample Conditions | wt % OPP | % OPP degradation | wt % OBPCP | % OBPCP degradation |
|---|---|---|---|---|---|
| A | Non irradiated | 5.81 | — | 12.65 | — |
| A | Irradiated | 5.76 | 0.86 | 12.51 | 1.11 |
| B | Non irradiated | 5.80 | — | 12.64 | — |
| B | Irradiated | 5.72 | 0.69 | 12.43 | 1.66 |
| C | Non irradiated | 5.80 | — | 12.65 | — |
| C | Irradiated | 5.72 | 0.69 | 12.64 | 0.08 |
| D | Non irradiated | 5.98 | — | 10.04 | — |
| D | Irradiated | 5.85 | 2.17 | 9.93 | 1.10 |
| E | Non irradiated | 5.98 | — | 13.08 | — |
| E | Irradiated | 5.85 | 2.17 | 12.91 | 1.30 |
| F | Non irradiated | 6.02 | — | 13.12 | — |
| F | Irradiated | 5.92 | 1.66 | 12.98 | 1.07 |
| G | Non irradiated | 6.01 | — | 13.11 | — |
| G | Irradiated | 5.89 | 2.16 | 12.98 | 1.14 |
| H | Non irradiated | 6.01 | — | 13.07 | — |
| H | Irradiated | 5.96 | 0.83 | 12.95 | 0.92 |
| I | Non irradiated | 6.02 | — | 10.10 | — |
| I | Irradiated | 5.94 | 1.33 | 10.11 | −0.10 |
| J | Non irradiated | 6.05 | — | 10.11 | — |
| J | Irradiated | 5.95 | 1.65 | 9.98 | 1.29 |
| K | Non irradiated | 6.14 | — | 10.15 | — |
| K | Irradiated | 6.06 | 1.30 | 10.01 | 1.38 |

The degradation of OPP was higher in the Samples D, E, F, and G that have hexylene glycol in the formula than in Samples A, B, C, H, I, J, and K that does not have hexylene glycol in the formula.

In summary, significant advantages of the present invention include broad spectrum microbial efficacy with normal concentrations, superior efficacy with typical or normal concentrations against *Mycobacterium smegmatis*; and good stability with respect to gamma-irradiation (low degradation), so that the solutions can be utilized as sterile disinfectants for clean room applications, hard surfaces, and as a tuberculocide, a fungicide, a bactericide, or a virucide. Another advantage is that the compositions do not contain any para tertiary amylphenol (PTAP). That is, the present invention excludes or is essentially free of PTAP, and that if utilized, only very small amounts are contained in the formulations of the present invention, for example about 2.0 or less, about 0.1% by weight or less, desirably about 0.01% by weight or less, and preferably nil, that is no PTAP whatsoever.

The phenolic disinfectant solutions of the present invention are desirably useful with respect to cleaning hard surfaces as in hospital, clinics, and the like. Surfaces for which the composition is effective at removing or substantially reducing contamination include surfaces of instruments employed in medical, dental, and pharmaceutical procedure, surfaces of equipment used in the food and beverage processing industry and work surfaces, walls, floors, ceilings, fermentation tanks, fluid supply lines, and other potentially contaminated surfaces in hospitals, industrial facilities, research laboratories, and the like. Particular examples include disinfection or sterilization systems, formulation of pharmaceuticals, medicaments, and cleaning agents having antifungal, antiviral, antituberculoidal, and antibacterial efficacy.

While in accordance with the Patent Statutes, the best mode and preferred embodiments have been set forth, the scope of the invention is not limited thereto, but rather, by the scope of the attached claims.

What is claimed is:

1. A low pH, gamma-irradiation stable, concentrated phenolic disinfectant solution comprising:
    ortho phenylphenol in an amount of about 1% to about 15% by weight, or ortho-benzyl parachlorophenol in an amount of about 2% to about 25% by weight, or optionally para-chloro-meta-cresol in an amount of about 1% to about 15% by weight, or any combination thereof;
    at least one hydrotropic surfactant;
    at least one hydrophilic acidic surfactant;
    at least about 5% by weight of a phosphoric acid;
    one or more aliphatic alcohols having from $C_1$ to $C_6$ atoms; and
    water, wherein the amount thereof is the weight difference of all other components and 100 wt. %;
    wherein said phenolic disinfectant solution has a pH of from about 0.5 to about 4.0, and is essentially free of para tertiary amylphenol;
    wherein said phenolic solution is essentially free of an emulsion surfactant, and a solubitizing surfactant; and
    wherein the amount of the above components are percent by weight based upon the total weight of said concentrated phenolic disinfection solution.

2. The phenolic disinfectant solution of claim 1, wherein said hydrotrope surfactant comprises sodium xylene sulfonate in an amount of from about 2% to about 25% by weight, sodium caprylyl sulfonate in an amount of from about 1% to about 30% by weight, sodium octyl sulfate in an amount of from about 1% to about 30% by weight, or any combination thereof;
    wherein said hydrophilic acidic surfactant comprises dodecyl benzene sulfonic acid in an amount of from about 1% to about 12% by weight;
    wherein the amount of said phosphoric acid is from about 5% to about 30% by weight; and
    wherein said solution is essentially free of a glycol and a polyglucoside.

3. The phenolic disinfectant solution of claim 2, wherein the total amount of said one or more alcohols is from about 2% to about 20% by weight,
    wherein any amount of said para tertiary amylphenol is about 2.0% by weight or less;
    wherein the amount of any said emulsion surfactant and solubilizing surfactant is less than about 2.0% by weight; and
    wherein the total amount of any said glycol or said polyglucoside is less than about 4.0% by weight.

4. The phenolic disinfectant solution of claims 3, wherein said phenolic disinfectant comprises said ortho phenylphenol in an amount of from about 2% to about 10% by weight, or said ortho benzyl parachlorophenol in an amount of from about 5% to about 20% by weight, or both;
    wherein said hydrotrope surfactant comprises said sodium xylene sulfonate in an amount of from about 4% to about 20% by weight, said sodium caprylyl sulfonate in an amount of from about 10% to about 27% by weight, said sodium octyl sulfate in an amount of from about 10% to about 27% by weight, or any combination thereof;
    wherein said alcohol comprises one or more of ethyl alcohol, propyl alcohol, or isopropyl alcohol, or any combination thereof in a total of amount of from about 2% to about 18% by weight;
    wherein said pH is from about 0.5 to about 2.0;
    wherein the amount of said phosphoric acid is from about 5% to about 25% by weight;
    wherein said amount of said glycol and said polyglucoside is less than about 2.0% by weight; and
    wherein the total amount of said emulsion surfactant and solubilizing surfactant is less than about 1% by weight.

5. The phenolic disinfectant solution of claim 4, wherein the amount of said orthobenzyl parachlorophenol is from about 8% by weight to about 18% by weight; wherein the total amount of any said glycol and said polyglucoside is less than about 0.1% by weight;
    wherein said hydrophilic acidic surfactant comprises said dodecyl benzene sulfonic acid in an amount of from about 3% to about 8% by weight;
    wherein the amount of said phosphoric acid is from about 10% to about 22% by weight;
    wherein said alcohol is said isopropyl alcohol in an amount of from about 5% to about 15% by weight; and
    wherein the amount of said para tertiary amylphenol is about 0.1% by weight or less.

6. The phenolic disinfectant solution of claim 1, that is stable to gamma-irradiation.

7. The phenolic disinfectant solution of claim 4, that is stable to gamma-irradiation of about 45 kGy, and is sterile.

8. The phenolic disinfectant solution of claim 2, that has reduced log reduction time with respect to *Mycobacterium smegmatis* and *Mycobacterium bovis*, as compared to a similar phenolic disinfectant containing para tertiary amylphenol.

9. The phenolic disinfectant solution of claim 5, that has reduced log reduction time with respect to *Mycobacterium smegmatis* and *Mycobacterium bovis*, as compared to a similar phenolic disinfectant containing para tertiary amylphenol.

10. A process for making a low pH, gamma-irradiation stable, concentrated phenolic disinfectant solution, comprising the steps of:
    adding together and mixing components comprising;
    a phenolic disinfectant comprising ortho phenylphenol in an amount from about 1% to about 15% by weight, ortho-benzyl parachlorophenol in an amount from about 2% to about 25% by weight, or parachloro-meta-cresol in an amount from about 1% to about 15% by weight, or any combination thereof;
    at least one hydrotropic surfactant;
    at least one hydrophilic acidic surfactant;
    at least about 5% by weight of a phosphoric acid;
    one or more aliphatic alcohols having from $C_1$ to $C_6$ atoms; and water, wherein the amount thereof is the weight difference of all other components and 100 wt. %;

wherein the solution is essentially free of a glycol and a polyglucoside;

wherein said phenolic disinfectant solution is essentially free of an emulsion surfactant and a solubilizing surfactant;

wherein said phenolic disinfectant solution is essentially free of para tertiary amylphenol; and forming a phenolic disinfectant solution having a pH of from about 0.5 to about 4.0;

wherein the amounts of the above components are percent by weight based on the total weight of said concentrated phenolic disinfectant solution.

11. The process of claim 10, wherein said hydrotrope surfactant comprises sodium xylene sulfonate in an amount of from about 2% to about 25% by weight, sodium caprylyl sulfate in an amount of from about 1% to about 30% by weight, sodium octyl sulfate in an amount of from about 1% to about 30% by weight, or any combination thereof;

wherein said hydrophilic acidic surfactant comprises dodecyl benzene sulfonic acid in an amount of from about 1% to about 12% by weight; and wherein the amount of said phosphoric acid is from about 5% to about 30% by weight.

12. The process of claim 11, wherein said phenol disinfectant compound is said ortho phenylphenol in an amount of from about 2% to about 10% by weight, or said ortho benzyl parachlorophenol in an amount of from about 5% to about 20% by weight, or both;

wherein said alcohol comprises ethyl alcohol, propyl alcohol, or isopropyl alcohol, or any combination thereof, in a total amount of from about 2% to about 18% by weight;

wherein the amount of said phosphoric acid is from about 5% to about 25% by weight;

wherein the amount of said para tertiary amyl phenol is about 2.0% by weight or less;

wherein any amount of said emulsion surfactant and a solubilizing surfactant is less than 2.0% by weight; and wherein any amount of said glycol and said polyglucoside, is less than about 4.0% by weight.

13. The process of claim 12, wherein said alcohol is said isopropyl alcohol in an amount of from about 5% to about 15% by weight;

wherein said hydrotropic surfactant is said sodium xylene sulfonate in an amount of from 8% to about 15% by weight, said sodium caprylyl sulfonate in an amount of from about 13% to about 22% by weight, said sodium octyl sulfate in an amount of from about 13% to about 22% by weight, or any combination thereof;

wherein said hydrophilic acidic surfactant comprises said dodecyl benzyl sulfonic acid in an amount of from about 3% to about 8% by weight;

wherein the amount of said para tertiary amyl phenol is less than about 0.1% by weight;

wherein said amount of said glycol and said polyglucoside is less than about 2.0% by weight; and wherein said amount of said emulsion surfactant and said solubilizing surfactant is less than about 1.0% by weight.

14. The process of claim 13, wherein said phenol disinfectant compound is said ortho phenylphenol in an amount of from about 4% to about 8% by weight, and said orthobenzyl parachlorophenol in an amount of from about 8% to about 18% by weight.

15. The process of claim 13, wherein the amount of said phosphoric acid is from about 10% to about 22% by weight; and wherein said pH is about 0.5 to about 2.0.

16. The process of claim 12, wherein 1 part by volume of said concentrated phenolic disinfectant solution is diluted in from about 16 to about 512 parts by volume of water.

17. The process of claim 10, wherein said phenolic disinfectant solution is stable to gamma-irradiation.

18. The process of claim 13, wherein said phenolic disinfectant solution is stable to gamma-irradiation of about 45 kGy, and is sterile.

19. The process of claim 11, wherein said phenolic disinfectant solution is a hard surface disinfectant, or a tuberculocide, a fungicide, a bactericide, or a virucide.

20. The process of claim 13, wherein said phenolic disinfectant solution is a hard surface disinfectant, or a tuberculocide, a fungicide, a bactericide, or a virucide.

* * * * *